(12) United States Patent
Wang et al.

(10) Patent No.: US 9,442,189 B2
(45) Date of Patent: Sep. 13, 2016

(54) MULTICHANNEL UWB-BASED RADAR LIFE DETECTOR AND POSITIONING METHOD THEREOF

(75) Inventors: Jianqi Wang, Xi'an (CN); Xijing Jing, Xi'an (CN); Yang Zhang, Xi'an (CN); Hao Lu, Xi'an (CN); Yanfeng Li, Xi'an (CN); Zhao Li, Xi'an (CN); Teng Jiao, Xi'an (CN); Xiao Yu, Xi'an (CN)

(73) Assignee: THE FOURTH MILITARY MEDICAL UNIVERSITY, Xi'an, Shaanxi (CN)

( * ) Notice: Subject to any disclaimer, the term of this patent is extended or adjusted under 35 U.S.C. 154(b) by 678 days.

(21) Appl. No.: 14/357,773

(22) PCT Filed: Jun. 20, 2011

(86) PCT No.: PCT/CN2011/001022
§ 371 (c)(1),
(2), (4) Date: May 13, 2014

(87) PCT Pub. No.: WO2012/055148
PCT Pub. Date: May 3, 2012

(65) Prior Publication Data
US 2015/0054670 A1    Feb. 26, 2015

(30) Foreign Application Priority Data

Oct. 27, 2010 (CN) .......................... 2010 1 0520832
Oct. 27, 2010 (CN) .......................... 2010 1 0520833

(51) Int. Cl.
*G01S 13/10* (2006.01)
*G01S 13/18* (2006.01)
(Continued)

(52) U.S. Cl.
CPC ........... *G01S 13/0209* (2013.01); *A61B 5/024* (2013.01);
(Continued)

(58) Field of Classification Search
CPC ...... A61B 5/024; A61B 5/08; A61B 5/0816; A61B 5/103; A61B 5/11; A61B 5/02; A61B 5/0205; A61B 5/05; A61B 5/0507; G01S 7/02; G01S 7/41; G01S 7/415; G01S 13/02; G01S 13/0209; G01S 13/04; G01S 13/88; G01S 13/887; G01S 13/888; G01S 15/02; G01S 15/50; G01S 15/52; G01S 15/523; G01S 7/28; G01S 7/2806; G01S 13/50; G01S 13/56; G01S 13/58; G01S 13/74; G01S 13/79; H03M 1/12; H03M 1/50; H03M 3/30; H03M 3/458; H03M 3/466; H03M 3/468; H03M 3/47
USPC ......... 342/21, 22, 27, 28, 175, 192–197, 59, 342/89–103, 42, 176, 179; 600/300, 407, 600/430; 341/120, 126, 155, 156; 327/100, 327/231, 237
See application file for complete search history.

(56) References Cited

U.S. PATENT DOCUMENTS 3,448,451 A * 6/1969 Wilcox ................. G01S 7/2806
327/237

(Continued)

OTHER PUBLICATIONS

English translation of the International Search Report of Sep. 29, 2011 for PCT/CN2011/001022, retrieved from WIPO.INT.*

(Continued)

*Primary Examiner* — Bernarr Gregory

(57) ABSTRACT

A multichannel UWB-based radar life detector includes a transmitting antenna and three receiving antennas for forming three radar echo signal channels. A 2-dimensional positioning method thereof includes: a1) amplifying weak life signals of stationary human by the channels, providing an 8-point integration method with an interval of 4 points to radar echo signals by distance; then breaking the integrated signals for decomposition and reconstruction in such a manner that target echo signals and three distance signals are formed; providing digital filtering and differential to the target echo signals for amplifying the weak but useful life signals; a2) 1-dimensionally distinguishing the signals by distance, analyzing spatial frequency according to the filtered and differentiated target echo signals as well as the distance signals for obtaining three target projection signals in the three channels; and a3) identifying the 2-dimensional position information of the targets according to the projection signals, forming an image.

18 Claims, 11 Drawing Sheets

(51) Int. Cl.

| | | |
|---|---|---|
| *G01S 13/89* | (2006.01) | |
| *G01S 13/02* | (2006.01) | |
| *G01S 13/88* | (2006.01) | |
| *A61B 5/024* | (2006.01) | |
| *A61B 5/08* | (2006.01) | |
| *A61B 5/11* | (2006.01) | |
| *G01S 13/04* | (2006.01) | |
| *G01S 7/41* | (2006.01) | |
| *G01S 13/00* | (2006.01) | |

(52) U.S. Cl.
CPC ............... *A61B 5/0816* (2013.01); *A61B 5/11* (2013.01); *G01S 7/415* (2013.01); *G01S 13/04* (2013.01); *G01S 13/88* (2013.01); *G01S 13/888* (2013.01)

(56) References Cited

U.S. PATENT DOCUMENTS

| | | | | |
|---|---|---|---|---|
| 3,858,205 A | * | 12/1974 | Ross | G01S 13/0209 342/21 |
| 4,012,730 A | * | 3/1977 | Nicholls | G01S 15/523 342/28 |
| 4,152,701 A | * | 5/1979 | Mara | G01S 13/58 342/21 |
| 5,117,227 A | * | 5/1992 | Goeke | H03M 1/50 341/156 |
| 5,144,313 A | * | 9/1992 | Kirknes | G01S 13/79 342/42 |
| 5,448,501 A | * | 9/1995 | Hablov | A61B 5/0507 342/28 |
| 5,966,090 A | * | 10/1999 | McEwan | A61B 5/0507 342/28 |
| 6,031,482 A | * | 2/2000 | Lemaitre | G01S 13/56 342/22 |
| 6,208,286 B1 | * | 3/2001 | Rostislavovich | A61B 5/0507 342/195 |
| 6,621,448 B1 | * | 9/2003 | Lasky | G01V 3/12 342/176 |
| 7,242,333 B1 | * | 7/2007 | Wu | H03M 3/47 341/120 |
| 8,378,879 B2 | * | 2/2013 | Lewis | G01S 13/50 342/195 |
| 8,454,528 B2 | * | 6/2013 | Yuen | A61B 5/0205 600/407 |
| 2008/0074307 A1 | * | 3/2008 | Boric-Lubecke | G01S 13/888 342/28 |

OTHER PUBLICATIONS

English translation of the Written Opinion of the International Searching Authority of Sep. 19, 2011 for PCT/CN2011/001022, retrieved from WIPO.INT.*

* cited by examiner

MULTICHANNEL UWB-BASED RADAR LIFE DETECTOR AND POSITIONING METHOD THEREOF

CROSS REFERENCE OF RELATED APPLICATION

This is a U.S. National Stage under 35 U.S.C. 371 of the International Application PCT/CN2011/001022, filed Jun. 20, 2011, which claims priority under 35 U.S.C. 119(a-d) to CN 201010520833.2, filed Oct. 27, 2010 and CN 201010520832.8, filed Oct. 27, 2010.

BACKGROUND OF THE PRESENT INVENTION

1. Field of Invention

The present invention relates to a technical field of vital signs non-contact detection, and more particularly to a multichannel UWB-based, wherein the UWB refers to ultra wide band, radar life detector and a 2-dimensional positioning method thereof for multiple human targets.

2. Description of Related Arts

A radar life detector is a novel special radar combined radar technology with biomedical engineering technology, which can penetrate non-metallic media (such as brick walls and ruins) and provide non-contact and long-range detection of human vital signs such as breathing, heartbeat and body movement. Radar life detector technology is an emerging technology of detection vital signs of living bodies and belongs to a very important advanced technical field recognized by the international scientific community. Because the technology requires no restriction on the targets and no connection with contact electrodes, sensors, cables, etc., and can penetrate certain medias such as clothes, gauze, bricks, ruins, etc. from a certain distance for human identification and detection, the radar life detector is widely used with irreplaceable advantages in fields such as search and rescue of the buried people in a disaster, through-wall monitoring in a fight against terrorism and battlefield reconnaissance, especially in the fields of emergency rescue, counter-terrorism, etc.

Target identification ability and resolution of distance and angle are the two key research points in the field of the conventional radar life detector, which are also problems to be solved by the present invention. At present, A mature radar life detector system based on continuous wave radar mechanism can only tell whether there are people or not without target distance and angle information. And penetration ability thereof should be further improved. In view of the advantages of the ultra-wideband radar, non-contact human-detecting radar is researched by combining advanced ultra wide band technology in the world with non-contact life detection technology according to the present invention.

The conventional radar life detector technology is mainly for single target detection. Detection and positioning of multiple targets are limited to moving targets. So far, the field has not yet resolved identification and 2-dimensional positioning problems of multiple stationary human targets. Detection and positioning technology of multiple stationary targets is a new research direction and difficulty in international life detection field. The technology is the key to the radar life detector and limits a scope of application of the radar life detector. If the problem of detection and positioning of multiple stationary targets is solved, efficiency of non-contact life detection will be greatly improved for meeting the requirements of rapid detection and positioning of multiple targets in real utilization.

SUMMARY OF THE PRESENT INVENTION

An object of the present invention is to provide a multichannel UWB-based radar life detector and a positioning method thereof aiming at disadvantages of the conventional technology for 2-dimensional detection and positioning of multiple stationary human targets.

Accordingly, in order to accomplish the above objects, the present invention provides a multichannel UWB-based radar life detector, comprising:

a multichannel UWB-based radar life detector, comprising:
a UWB bio-radar front-end; and
a calculation unit;
wherein the UWB bio-radar front-end comprises:
a transmitting antenna;
three receiving antennas;
a pulse oscillator;
an electromagnetic pulse generator; and
a sampling integrator;
wherein the transmitting antenna respectively forms channels with the receiving antennas in such a manner that three the channels are formed; the pulse oscillator generates a pulse signal, the pulse signal stimulates the electromagnetic pulse generator for generating a narrow pulse and transmitting the narrow pulse through the transmitting antenna; a reflected signal of the narrow pulse is sent to the sampling integrator through the receiving antenna; the pulse signal generated by the pulse oscillator also passes through a time-delay circuit and a range gate generator for generating a range gate and selecting the reflected signal; the reflected signal is integrated by the sampling integrator and weak signals are detected; the weak signals are amplified by an amplifier and filtered by a filter for obtaining three radar echo signals; the radar echo signals are sampled by a high-speed A/D data acquisition card and sent to the calculation unit for analysis, in such manner that biological information and 2-dimensional position information of multiple human targets are finally obtained.

Preferably, the transmitting antenna is close to one of the receiving antennas and is placed in a center, the other receiving antennas are placed at two sides for forming a dumbbell-shaped structure.

Preferably, the calculating unit comprises:
a signal integration module;
a signal decomposition and reconstruction module;
a digital filtering module;
a digital differential module;
a spatial frequency analysis module; and
a filtered back projection positioning module;
wherein the signal integration module integrates the radar echo signals by distance; the signal decomposition and reconstruction module decomposes and reconstructs the integrated radar echo signals for forming three target echo signals and three distance signals; the digital filtering module and the digital differential module provide digital filtering and digital differential to the target echo signals; the spatial frequency analysis module analyzes spatial frequency according to the filtered and differentiated target echo signals as well as the distance signals for obtaining three projection signals of the targets; the filtered back projection positioning module identifies the 2-dimensional position information of the targets according to the projection signals and forms an image.

Preferably, the multichannel UWB-based radar life detector further comprises: a projection signal pretreatment module for averaging and normalizing the projection signals before sending the pretreated projection signals to the filtered back projection positioning module.

Preferably, the filtered back projection positioning module comprises:
a 1-dimensional Fourier transform module;
a 1-dimensional weighting factor module;
a 1-dimensional inverse Fourier transform module; and
a direct back projection module;
wherein the 1-dimensional Fourier transform module applies 1-dimensional Fourier transform on the pretreated projection signals; the 1-dimensional weighting factor module multiplies the transformed projection signals by a 1-dimensional weighting factor $|\rho|$; the 1-dimensional inverse Fourier transform module applies 1-dimensional inverse Fourier transform on the multiplied projection signals; the direct back projection module directly projects the inversely transformed projection signals.

Preferably, the 1-dimensional weighting factor $|\rho|$ is finally defined as:

$$\begin{cases} |\rho| = 1 & 0.08 \text{ Hz} < F_1\{g_\theta(t)\} < 0.7 \text{ Hz} \\ |\rho| = 0 & F_1\{g_\theta(t)\} < 0.08 \text{ Hz or } F_1\{g_\theta(t)\} > 0.7 \text{ Hz} \end{cases},$$

wherein $g_\theta(t)$ is the pretreated projection signal of one of the channels, $F_1\{g_\theta(t)\}$ is the transformed projection signal.

Preferably, the multichannel UWB-based radar life detector further comprises: a smearing elimination module for eliminating smearing of the image formed by the filtered back projection positioning module.

Preferably, the smearing is eliminated by a method comprising: presetting a threshold of pixel value in a 2-dimensional display area, and coloring pixels with a value lower than t threshold by a background color.

Preferably, the image is displayed in a 2-dimensional pseudo color mode, distance and angle information is also displayed for positioning the multiple targets and displaying detection results.

A 2-dimensional positioning method of a multichannel UWB-based radar life detector for positioning the multiple human targets is also provided according to the present invention.

The multichannel UWB-based radar life detector comprises: a transmitting antenna and three receiving antennas for forming three radar echo channels; wherein the 2-dimensional positioning method comprises steps of:

a1) amplifying weak life signals of stationary human bodies by the channels, processing radar echo signals by distance with an 8-point integration method with an interval of 4 points; then breaking the integrated signals for decomposition and reconstruction in such a manner that target echo signals and three distance signals are formed; providing digital filtering and digital differential to the target echo signals for amplifying the weak but useful life signals;

a2) 1-dimensionally distinguishing the signals by distance, analyzing spatial frequency according to the filtered and differentiated target echo signals as well as the distance signals for obtaining three projection signals of the targets in the three channels; and a3) identifying the 2-dimensional position information of the targets according to the projection signals, forming an image.

Preferably, the transmitting antenna is close to one of the receiving antennas and is placed in a center, the other receiving antennas are placed at two sides for forming a dumbbell-shaped structure.

Preferably, the step a1) specifically comprises steps of:
a11) respectively integrating the radar echo signals by distance;
a12) decomposing and reconstructing the integrated radar echo signals for forming the three target echo signals and the three distance signals;
a13) providing the digital filtering and the digital differential to the target echo signals; and
a14) analyzing the spatial frequency according to the filtered and differentiated target echo signals as well as the distance signals for obtaining the three projection signals of the targets.

Preferably, the 2-dimensional positioning method further comprises a step of: pretreating the projection signals, which is provided before the step a2), for averaging and normalizing the projection signals.

Preferably, the step a3) specifically comprises steps of:
a31) applying 1-dimensional Fourier transform on the pretreated projection signals;
a32) multiplying the transformed projection signals by a 1-dimensional weighting factor $|\rho|$;
a33) applying 1-dimensional inverse Fourier transform on the multiplied projection signals; and
a34) directly projecting the inversely transformed projection signals.

Preferably, the 1-dimensional weighting factor $|\rho|$ in the step a32) is finally defined as:

$$\begin{cases} |\rho| = 1 & 0.08 \text{ Hz} < F_1\{g_\theta(t)\} < 0.7 \text{ Hz} \\ |\rho| = 0 & F_1\{g_\theta(t)\} < 0.08 \text{ Hz or } F_1\{g_\theta(t)\} > 0.7 \text{ Hz} \end{cases},$$

wherein $g_\theta(t)$ is the pretreated projection signal of one of the channels, $F_1\{g_\theta(t)\}$ is the transformed projection signal.

Preferably, the 2-dimensional positioning method further comprises: a smearing elimination step for eliminating smearing of the image.

Preferably, the smearing is eliminated by a method comprising: presetting a threshold of pixel value in a 2-dimensional display area, and coloring pixels with a value lower than the threshold by a background color.

Preferably, the image is displayed in a 2-dimensional pseudo color mode, distance and angle information is also displayed for positioning the multiple targets and displaying detection results.

Therefore, advantages of the present invention are as follows:

1) amplification of weak vital signs, human identification and 1-dimensional distance distinction are provided before the 2-dimensional positioning, which is a new method of the radar life detector for positioning multiple human targets;

2) a reshaping time-frequency analysis method is utilized, wherein the echo signals acquired by a single-channel UWB-based radar life detector system are decomposed, reconstructed and relatively treated with a 1-dimensional distance distinction algorithm mainly based on spatial frequency analysis, which may provide a new method for the 1-dimensional distance distinction of the multiple stationary targets in life detection; and 3) a preferred antenna array structure, which is a dumbbell-shaped structure, is provided; detecting with the structure provides a best multiple targets positioning effect with least antennas and a simplest structure.

These and other objectives, features, and advantages of the present invention will become apparent from the following detailed description, the accompanying drawings, and the appended claims.

DETAILED DESCRIPTION OF THE PREFERRED EMBODIMENT

Figure 1:
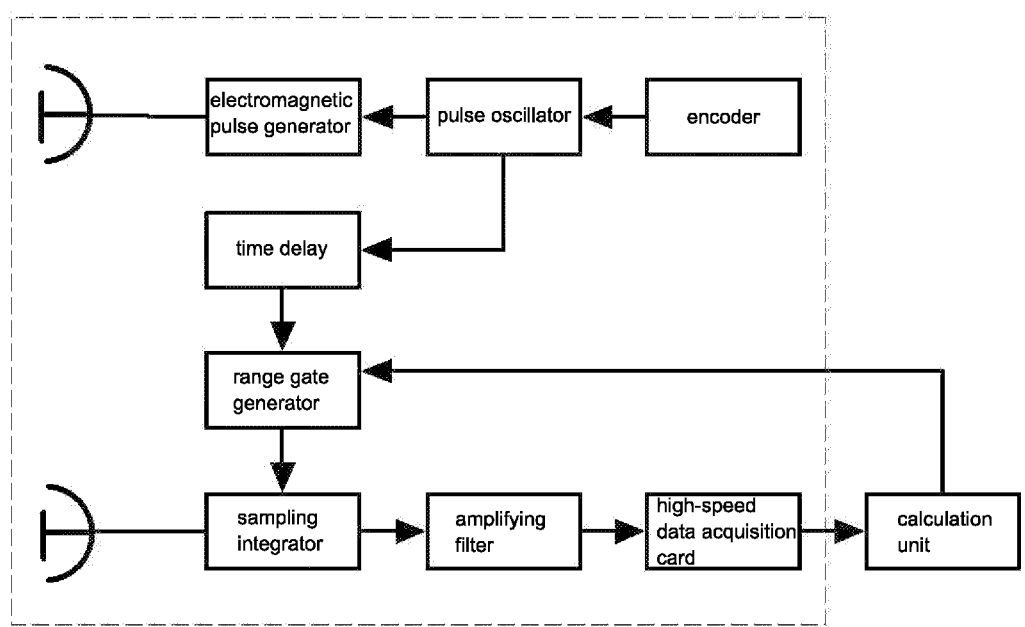
FIG. 1 is a schematic view of a single-channel UWB-based radar life detector system according to the present invention.

Referring to the drawings and preferred embodiments, the present invention is further illustrated.

Preferred Embodiment 1

In the preferred embodiment 1, only one channel of the channels is illustrated as an example. Referring to FIG. 1 of the drawings, a schematic view of a single-channel UWB-based radar life detector system according to the present invention is illustrated, wherein a pulse oscillator generates a pulse signal, the pulse signal stimulates an electromagnetic pulse generator for generating a narrow pulse and transmitting the narrow pulse through the transmitting antenna; a reflected signal of the narrow pulse is sent to the sampling integrator through the receiving antenna; the pulse signal generated by the pulse oscillator also passes through a time-delay circuit for generating a range gate and selecting the reflected signal; the reflected signal is integrated by the sampling integrator and weak signals are detected after thousands of the pulses are accumulated; the weak signals are amplified by an amplifier and filtered; then the radar echo signals are sampled by a high-speed data acquisition card and sent to the calculation unit for analysis and identification; at last, target distance is calculated.

Referring to the FIG. 1 of the drawings, a radar front-end is in a dashed box. A center frequency and a bandwidth of the system are all 500 MHz. A wave coverage angle is 60°. A calculation unit controls a range gate for obtaining the echo signals from different distances in a detection area.

Figure 3:
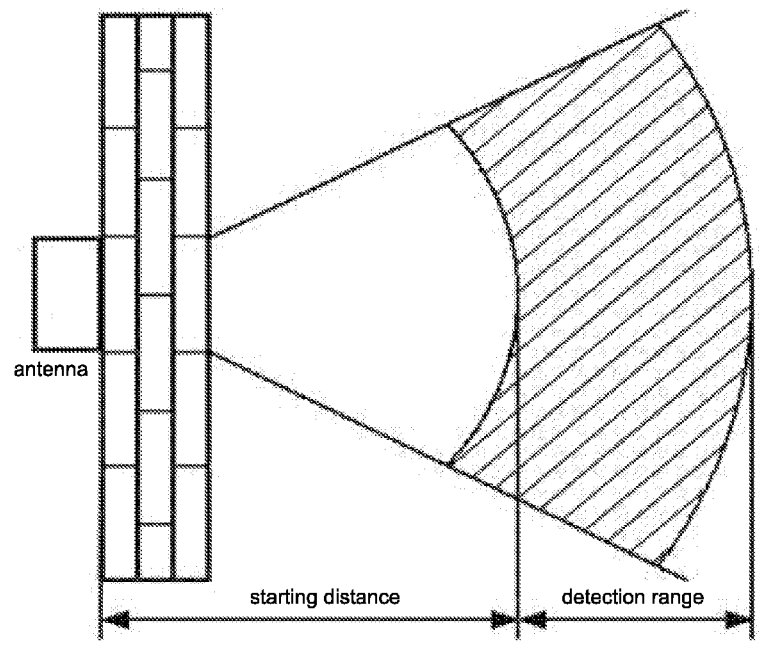
FIG. 3 is a sketch view of parameter setting of a UWB-base radar according to the present invention.

Parameters controllable by a computer are a start distance, a detection range, a sampling frequency and an antenna gain. Referring to FIG. 3 of the drawings, after signals from the antenna pass through a brick wall, a fan-shaped detection area is formed. By setting the start distance and the detection range, the fan-shaped area, which is a shadowed area as shown in the FIG. 3, is scanned. If target information is detected after analyzing the echo signals, it can be concluded that the target is in the fan-shaped area. By continuously adjusting the start distance, tomography is provided within a certain area. By adjusting the detection range (without changing a number of received points of the antenna), sensitivity of the system is adjusted and target resolution ratio is changed for providing rough scan and fine scan within a certain area.

For example, the start distance is set to 6 m (40 ns), the detection range is set to 3 m (20 ns) and the echo signal is a sequence comprising 2048 points. Then an effective detection area of the radar is a 60° fan-shaped area 6 m~9 m in front of the antenna. The echo signal only represents longitudinal information within 3 m, wherein the 3 m is evenly divided into the 2048 parts in such a manner that 2048 data are acquired. The 2048 data are called the 2048 points, and the No. n point represents a distance of:

$$s = 6 + \frac{n}{2048} \times 3 (m) \qquad (1)$$

wherein n is a number of the point.

According to Nyquist-Shannon sampling theorem, the sampling frequency must be twice higher than a highest frequency of the signal. The A/D (analog/digital) sampling frequency is set to 64 Hz.

Figure 2:
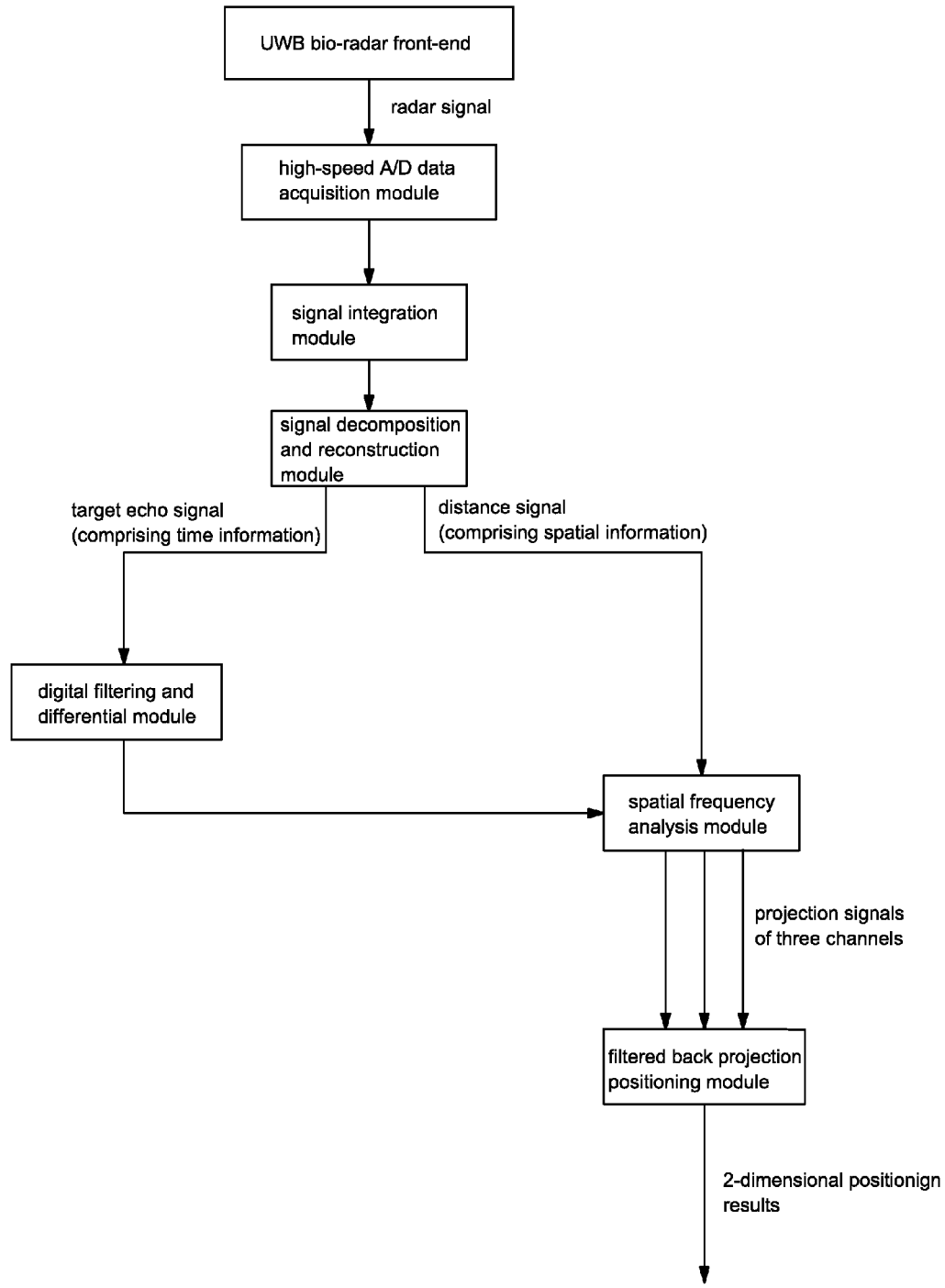
FIG. 2 is a schematic view of a multichannel UWB-based radar life detector system according to the present invention.

Referring to FIG. 2 of the drawings, a schematic view of a multichannel UWB-based radar life detector system according to the present invention is illustrated, wherein the calculating unit comprises:

a signal integration module;
a signal decomposition and reconstruction module;
a digital filtering module;
a digital differential module; and
a spatial frequency analysis module;

wherein the signal integration module integrates the radar echo signals by distance; the signal decomposition and reconstruction module decomposes and reconstructs the integrated radar echo signals for forming target echo signals and distance signals; the digital filtering module and the digital differential module provide digital filtering and digital differential to the target echo signals; the spatial frequency analysis module analyzes spatial frequency according to the filtered and differentiated target echo signals as well as the distance signals for obtaining target 1-dimensional distances.

Preferred Embodiment 2

In the preferred embodiment 2, only one channel of the channels is illustrated as an example for illustrating an amplification method of weak signals of stationary targets.

For identifying the stationary human targets, the weak life signals thereof are amplified at first. In the preferred embodiment 2, according to characteristics of the UWB-based radar echo signal, the signals sampled with a high speed are treated and useful signals thereof are amplified by a weak biomedical signal treatment method for improving a signal-to-noise ratio and basically identifying the human targets.

The amplification method comprises: processing radar echo signals by distance with an 8-point integration method with the interval of 4 points; then breaking the integrated signals for decomposition and reconstruction in such a manner that target echo signals and distance signals are formed; providing digital filtering and digital differential to the target echo signals for amplifying the weak but useful life signals.

2-1) Signal Integration

The sampling frequency of the high-speed data acquisition card is 64 Hz according to the preferred embodiment 2. A large amount of data are generated by the A/D sampling, which is not conducive to real-time computing. Otherwise, decreasing the data too much will lead to a result that the echo signals lack distance information. Therefore, the radar echo signals are piecewise-integrated by the 8-point integration method with the interval of 4 points according to the preferred embodiment 2 while distance resolution ratio is high enough.

The 8-point integration method with the interval of 4 points is adding every 8 points of the data together and averaging the results, then integrating once every 4 points (for example, integrating points 0~7, 4~11, 8~15 and so on), in such a manner that the sampled data is ¼ of the original signal after being integrated by distance. The sequence of the signals is shortened without losing signal characteristics. A computation amount is reduced and computation speed is improved.

2-2) Decomposition and Reconstruction of the Signals

Figure 4:
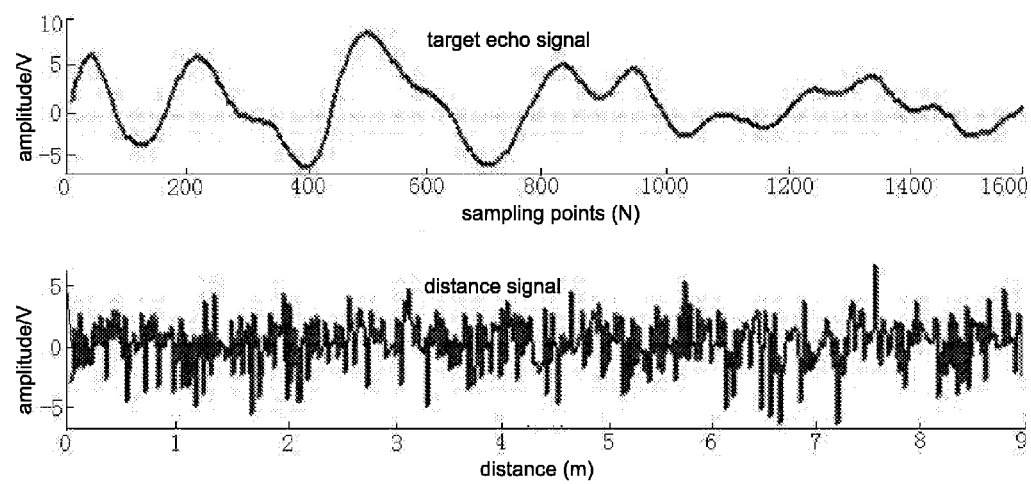
FIG. 4 is waveforms of a target echo signal and a distance signal according the present invention.
Figure 5:
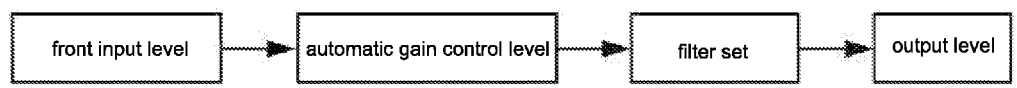
FIG. 5 is a schematic view of a hardware filtering circuit according to the present invention.

The integrated signals are decomposed and reconstructed according to a time domain and a space domain for forming the target echo signals x(t) with time information and the distance signals y(d) with distance information, wherein the t is a time variable, the d is a distance variable. The target echo signals represent time-related signal amplitude of the points corresponding to distance. An abscissa of the target echo signals represents time. The distance signals are a sequence comprising points with same distances and same amplitudes at a same time. An abscissa of the distance signals represents distance. Referring to FIG. 4 of the drawings, waveforms of a randomly selected target echo signal (1600 points, 25 s) and a distance signal (60 ns, 9 m) are illustrated.

The target echo signals improve the signal-to-noise ratio and are conducive to extraction of the vital sign signals. The distance signals not only greatly decrease the computation amount, but also ensure suitable distance resolution ratio.

2-3) Filter Selection 2-3-1) Hardware Filter

A filter bandwidth is adjustable before the hardware filter is connected to the high-speed A/D data acquisition card according to the preferred embodiment 2. During a preliminary experiment, filters with bandwidths of 0.08~10 Hz, 0.08~100 Hz, 0.08~1000 Hz, 0.08~2000 Hz, 0.08~3000 Hz, 0.08~4000 Hz and 0.08~5000 Hz are tested. The bandwidth of 0.08~5000 Hz is utilized according to an effect comparison. The gain has two levels, wherein when the gain is 1, amplification multiple is 1; when the gain is 2, the amplification multiple is 2.

A single-channel UWB-based system without the hard filter, a single-channel UWB-based system with the hard filter (wherein the gain is 1) and a single-channel UWB-based system with the hard filter (wherein the gain is 2) are utilized for randomly acquiring 16 sets of data (without target or with single target) from each of the systems, wherein 48 sets of the data are acquired totally. The 48 sets of data are treated and identified respectively by algorithms of the calculation unit for counting identification accuracy. Counting results are shown in Table 1.

TABLE 1 identification accuracy with and without hardware filter (48 sets of data)

| utilization of hardware filter | without hard ware filter | gain = 1 | gain = 2 |
|---|---|---|---|
| accuracy | 50% | 62% | 44% |

The accuracy of the hard filter with the gain of 1 is 62%, which is the highest.

According to the comparison, when the gain is 1 and the bandwidth is 0.08~5000 Hz, a detection effect of the UWB-based system with the hard filter is the best.

2-3-2) Digital Filter

Phase information of the weak vital sign signals is very important for stationary target detection. And the stationary target detection and 1-dimensional distinction technology have a high requirement of algorithm stability and subsequent digital signal treatment. Therefore, high-frequency interference is filtered by a finite impulse response (FIR) filter for extracting the useful signals such as breathing. A system function of the FIR filter is:

$$H(z) = \sum_{n=0}^{N-1} h(n)z^{-n}, 0 \le n \le N-1 \quad (2)$$

A difference equation thereof is:

$$y(n) = \sum_{k=0}^{N-1} b_k x(n-k) \quad (3)$$

An amplitude-frequency characteristic of the filter is directly affected by an order thereof. The more the orders are, the better the amplitude-frequency characteristic and filtering effects will be. However, increasing the order without limitation has some negative effects such as increasing the system computation amount and extending time delay of filter outputs. According to the above two aspects, An FIR filter with 160 orders is tested within the system computation capability.

The filter utilizes window functions. After comparing amplitude-frequency characteristics of filters with different window functions, Hamming window is finally utilized.

Respiratory rate of a human under normal conditions is 15~20 times per minute, and the respiratory rate of a human under abnormal conditions is not higher than 0.4 Hz. Therefore, a digital filter is utilized, and a cut-off frequency thereof is mainly relative to 0.4 Hz. That is to say, the echo signals are filtered by a low-pass filter whose cut-off frequency is not lower than 0.4 Hz for comparing performances of different filters. Low-pass filters with cut-off frequencies of 0.4 Hz, 0.5 Hz, 0.6 Hz, 0.7 Hz and 0.8 Hz are tested.

48 sets of data are randomly acquired respectively with detection ranges (which are radar windows) of 20 ns (3 m) and 60 ns (9 m), wherein 96 sets of data are acquired totally. During a comparison experiment, software and hardware parameters are not changed except cut-off frequency of the filter for counting identification accuracy. Counting results are shown in Table 2.

TABLE 2 identification accuracy with different cut-off frequencies

| accuracy (%) | 0.4 Hz | 0.5 Hz | 0.6 Hz | 0.7 Hz | 0.8 Hz |
|---|---|---|---|---|---|
| 20 ns | 56.25 | 62.50 | 62.50 | 62.50 | 62.50 |
| 60 ns | 43.75 | 45.83 | 31.25 | 27.08 | 31.25 |

According to the above results and the comparison, the high-frequency interference is finally filtered by the Hamming FIR digital filter with 160 orders and the cut-off frequency of 0.5 Hz for keeping the vital sign signals such as breathing.

2-4) Differentiator Selection

Because of a DC (direct current) component and baseline drift, the echo signals usually comprise extreme-low frequency parts with great energy. Therefore, the signals seriously drift from a baseline and significantly affect the weak vital sign signals. The DC component and extreme-low frequency interference are filtered by digital differential by time according to the preferred embodiment 2 in such a manner that the useful signals fluctuate around a zero baseline for amplifying the vital sign signal such as breathing. A calculation procedure of the differentiator is shown in a following formula (4):

$$y(n) = x(n) - \frac{\sum_{k=n-m}^{n-1} x(k)}{m} \quad (4)$$

Wherein the y is an output signal, the x is an input signal, the m is the order and the n is the number of the point.

48 sets of data are randomly acquired respectively with detection ranges (which are radar windows) of 20 ns (3 m) and 60 ns (9 m), wherein 96 sets of data are acquired totally. The signals are sampled signals (without target or with single target) of the single-channel UWB-based system. The data are integrated by digital differentiators with 20 orders, 40 orders, 60 orders, 80 orders, 100 orders, 120 orders, 140 orders, 160 orders and 180 orders for identification and distance calculation. Accuracy of the digital differentiators is shown in Table 3.

TABLE 3 identification accuracy with different digital differentiator orders

| accuracy (%) | 20 orders | 40 orders | 60 orders | 80 orders | 100 orders | 120 orders | 140 orders | 160 orders | 180 orders |
|---|---|---|---|---|---|---|---|---|---|
| 20 ns | 62.50 | 56.25 | 77.08 | 70.83 | 70.83 | 70.83 | 70.83 | 68.75 | 68.75 |
| 60 ns | 43.75 | 31.25 | 43.75 | 31.25 | 37.50 | 41.67 | 41.67 | 43.75 | 43.75 |

It can be concluded that the identification accuracy of the signals treated by the digital differentiator with 60 orders is the highest. Average accuracy of the 96 sets of the data is 60.78%. According to the comparison, the DC component and the extreme-low frequency interference are filtered by the digital differentiator with 60 orders according to the preferred embodiment 3 for amplifying the vital sign signal.

Figure 6:
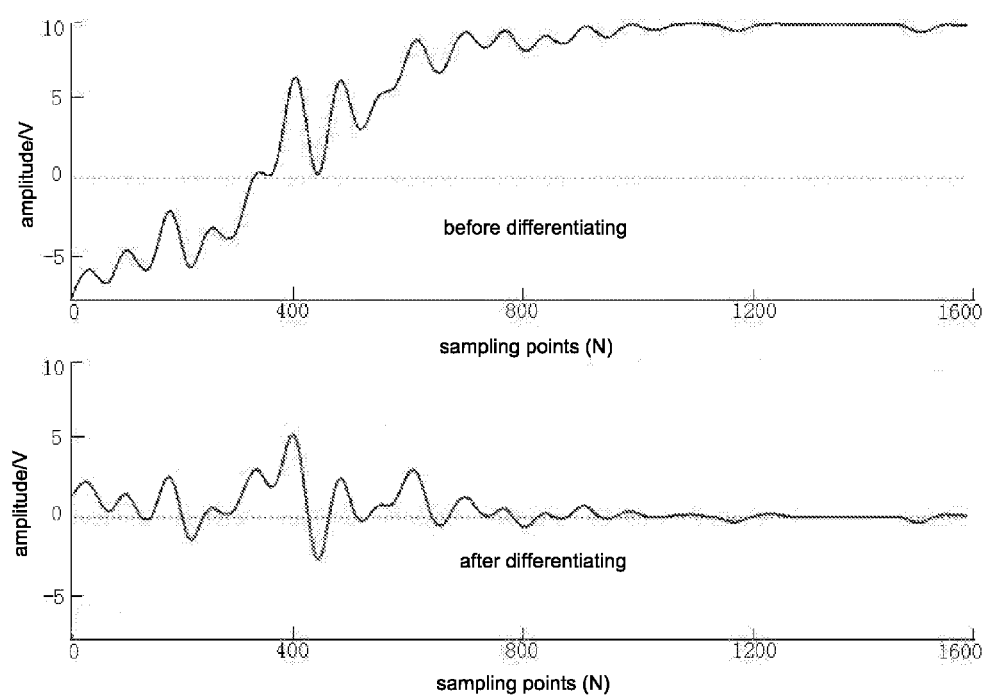
FIG. 6 is a comparison diagram of signal waveforms before and after being treated with a differential algorithm according to the present invention (wherein date of 30-second signals are shown).

Referring to FIG. 6 of the drawings, after the target echo signals are differentiated with 60 orders by time, the signals move to and closely fluctuate around a zero baseline in such a manner that the DC component and the extreme-low frequency interference are filtered and the useful signals are amplified.

Preferred Embodiment 3

In the preferred embodiment 3, only one channel of the channels is illustrated as an example for illustrating 1-dimensional distance distinction and spatial frequency analysis.

After the stationary target echo signals are amplified, the human targets will be distinguished in distance. The distance signals are ultra-low frequency signals reflecting distance information. Therefore, relating to characteristics that the distance signal comprises spatial information and is not stable, a space-frequency joint distribution function is formed. The distance signals are analyzed by space-frequency joint analysis (which is modified time-frequency analysis) for representing density and intensity of energy with different distances and frequencies, in such a manner that distance information of each of the human targets are illustrated.

The time-frequency analysis represents variation of a signal frequency spectrum according to a time axis. When the time variable is replaced by the distance variable, results of the time-frequency represent spatial variation of the frequency spectrum. Spectrum analysis of targets with different distance is provided by taking advantage of the above characteristic of the time-frequency analysis for obtaining human identification results and 1-dimensional distance information of the targets. Thus, a new application method of space-frequency joint analysis is formed. Essence thereof is still the time-frequency analysis.

The time variable in the time-frequency analysis is replace by the space (distance) variable according to the preferred embodiment 3 for forming a space-frequency joint distribution function in such a manner that the energy density is represented by both the space and frequency information. With the above method, a positioning function of space and frequency is provided for providing a significant frequency estimating method for unstable signals with a certain range.

Time-frequency transform comprises unilinear transform such as short-time Fourier transform, and bilinear transform such as Wiener-Ville distribution and wavelet transform. The spatial frequency transform is provided by replacing the time variable of the time-frequency analysis by the space (distance) variable according to the preferred embodiment 3. Distance resolution ratio thereof is predetermined and does not need to be changed by varying a window width. Testing targets are still the human body. The breathing signals thereof are relatively stable in a long period of time. The breathing signal belongs to along unstable signal with stable parts. The above type of signals is suitable for being analyzed by the short-time Fourier transform. Therefore, the spatial frequency is analyzed by short-time Fourier transform of the unilinear transform according to the preferred embodiment 3. Results thereof are analyzed and compared.

The differentiated distance signal with a time window of 60 ns (corresponding to a detection range of 9 m and the starting distance of 1 ns) is evenly divided into 100 sections in distance according to the preferred embodiment 3. A corresponding distance resolution ratio is around 0.09 m. For eliminating interference of antenna direct wave, the first 12 points of the distance signal are abandoned and are not divided. The other 500 points are divided into 100 sections Amplitudes of the 5 points of each the section are added together and a result thereof represents a value of the section. And a new distance signal with 100 values is formed. The 100 values are corresponding to the evenly distributed target echo signal started from 12×9/512=0.21 m and ended at 9 m.

After the division, new distance information in the section is extracted once every 10 s, wherein the positioning result refresh rate is needed for actual detection. A total of 64×10=640 new distance signals are acquired (with the sampling rate of 64). Each of the distance signals are split into points (100 points). Then the points are reorganized according to time sequence for forming a new target echo signal comprising time information (wherein 100 sets of the target echo signals are acquired totally). The new target echo signals are placed end to end from the nearest signal to the farthest signal according to the antenna for forming an input signal of the spatial frequency analysis.

The spatial frequency analysis is provided to the input signal in such a manner that the input signal is transformed by the short-time Fourier transform, wherein the window width is corresponding to length of the new target echo signal, which is defined as 64×10=640. Each window sliding distance is corresponding to the distance resolution ratio of the distance signal. According to a principle that an amount of transform points should be no less than the window width and a requirement for frequency resolution ratio raised by the identification results, the amount of the Fourier transform points is selected to be 1024. After the above parameters are determined, the short-time Fourier transform is provided to the input signal, and results thereof are drawn. A short-time Fourier transform formula is illustrated as a following formula (5):

$$STFT(t,w) = \int S(\tau)\gamma(\tau-t)e^{-jw\tau}d\tau \qquad (5)$$

wherein the $S(\tau)$ is the input signal, the $\gamma(\tau)$ is the window function.

In selection of length of the window function, in order to improving time resolution ratio of the short-time Fourier transform, time width of the window function is required to be as short as possible. On the other hand, for ensuring a high frequency resolution ratio of the short-time Fourier transform, the time width of the window function is required to be as long as possible. Therefore, improvement of the time resolution ratio contradicts improvement of the frequency resolution ratio. Practically, the width of the window function $\gamma(\tau)$ should be corresponding to length of the stable part of the signal. In the experiment, a normal breathing frequency of the human targets to be tested is 15~20 times per minute. That is to say, a complete respiratory movement took 3~4 s. In order to reduce uncertain factors of the human respiratory and impacts of individual difference for ensuring suitable frequency resolution ratio, time width of the window function is selected to be 10 s. A corresponding window width in spatial frequency analysis is 640.

Preferred Embodiment 4

In the preferred embodiment 3, only one channel of the channels is illustrated as an example for illustrating a peak discrimination method and a threshold setting method.

Results of the space-frequency analysis are a 3-dimensional (space, frequency and energy) corresponding relationship. Two coordinate axes respectively represent distance and frequency, and the energy intensity is represented by depth of colors. By utilizing an appropriate method and setting a suitable threshold of vital sign identification, distance distinction and calculation of the multiple stationary targets can be provided by the single-channel. If at a certain distance, the signal energy is high, peaks are concentrated, the signal energy is significantly higher than the signal energy at the neighboring distance, and the signal energy is in accordance with the threshold, then the stationary human target exists at the corresponding distance within the detection range of the receiving antenna (wherein the 1-dimensional distance is detected). If a large amount of energy accordance with the threshold exists at a plurality of distances, then a plurality of the stationary human targets exist at the distances. The 1-dimensional distance values of the targets are recorded by the algorithm for obtaining distance from the target to the antenna.

Figure 7:
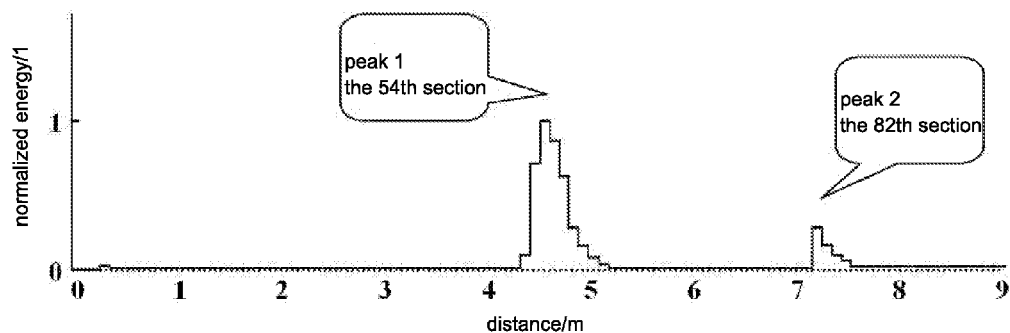
FIG. 7 is a result of peak discrimination applied on double-target data according to the present invention.

Multiple targets identification and distance calculation comprise steps of:

finding 15 sections with the highest energy values out of the 100 selections, and identifying all the energy peaks of the 15 sections; marking the energy peaks as $E_{peak1}$, $E_{peak2}$, $E_{peak3}$ and so on according to the energy value; wherein the energy peak is defined as: the energy value of the section is higher than the energy values of the adjacent sections; recording order numbers of the sections with the energy peaks after finding the energy peaks for calculating the target distance;

calculating an average value of the 10 sections with the lowest energy values and marking as $E_{mean}$, comparing the energy peaks with the average value of the 10 sections with the lowest energy values for identifying the number of the targets; wherein comparison thresholds are as follows:

(1) if the $E_{peak1}$ is higher than four times of the $E_{mean}$, that is to say, $E_{peak1} > 4E_{mean}$, the target exists at the section, the distance of the target is calculated from the order number of the section;

(2) if the $E_{peak2}$ is higher than three times of the $E_{mean}$, that is to say, $E_{peak2} > 3E_{mean}$, the target exists at the section, the distance of the target is calculated from the order number of the section; and (3) if the $E_{peak3}$ is higher than 2.5 times of the $E_{mean}$, that is to say, $E_{peak1} > 2.5E_{mean}$, the target exists a the section, the distance of the target is calculated from the order number of the section;

Referring to FIG. 7 of the drawings, a result of peak discrimination applied with thresholds on double-target data according to the present invention.

It can be concluded that the 100 sections of the signal had two energy peaks located at the 54th section and the 82th section. The energy values of the two peaks are compared with the thresholds thereof and the two peaks all represented the targets. After calculation, the distances of the two targets are: (54−1)×0.09+0.21=4.98 m and (82−1)×0.09+0.21=7.50 m.

Thus, the multiple stationary targets are identified and the distance thereof is calculated with each of the channels. That is to say, the 1-dimensional distance information of the multiple targets is obtained. Accordingly, relative treatments are provided on the 1-dimensional results of the three channels for generating 2-dimensional projection signals of the channels.

Preferred Embodiment 5

5-1) Angle Determination of Transceiver Antenna

Figure 8:
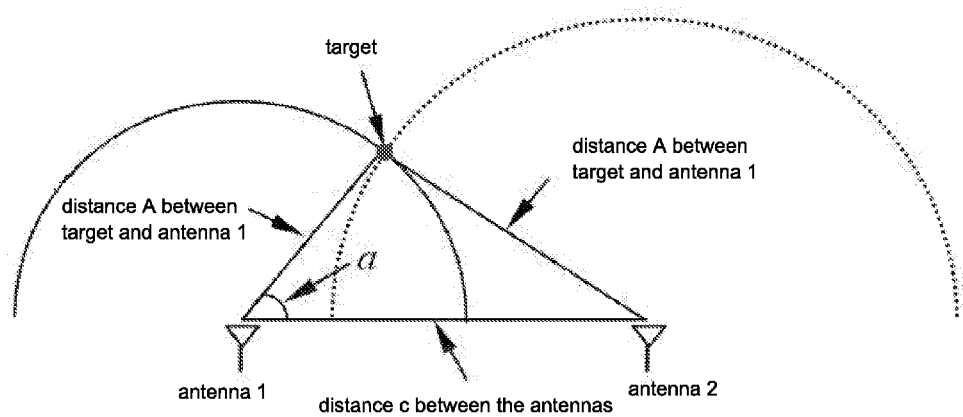
FIG. 8 is a sketch view of an angle determination algorithm according to the present invention.

For 2-dimensional positioning, angle information is needed besides the distance information. With the transceiver antenna, only cosine theorem is utilized for determining the angle. Referring to FIG. 8 of the drawings, a sketch view of an angle determination algorithm according to the present invention is illustrated.

The distance A between the target and a first antenna and the distance B between the target and a second antenna have been obtained by the distance distinction algorithm, the distance C between the first antenna and the second antenna is known. Therefore, according to a formula (6), an angle α between the target and the first antenna is obtained. Then the 2-dimensional positioning information is obtained by combining the distance and the angle in a polar coordinate.

$$2AC \cos \alpha = A^2 + C^2 - B^2 \quad (6)$$

5-2) Angle Determination of Bistatic Antenna

Figure 9:
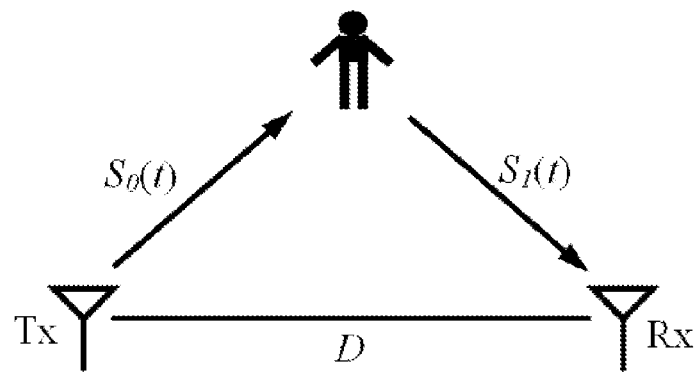
FIG. 9 is a sketch view of an electromagnetic wave transmission path with a bistatic antenna form according to the preset invention.

In a real multichannel system, the transmitting antenna and the receiving antenna are separated. Referring to FIG. 9 of the drawings, supposing that a distance between the transmitting antenna Tx and the receiving antenna Rx is D, a distance between the transmitting antenna Tx and the target is $S_0(t)$, and a distance between the receiving antenna Rx is $S_1(t)$. Then a electromagnetic wave transmitted by the transmitting antenna Tx will be received by receiving antenna Rx after a time of D/c (wherein the c refers to a speed of electromagnetic wave in the air). Therefore, direct waves, whose waveform is a straight line, exist in the echo signals received by the Rx. The direct waves comprise no target information and should be considered during signal treatments. Referring to FIG. 9 of the drawings, a sketch view of an electromagnetic wave transmission path with a bistatic antenna form according to the preset invention is illustrated.

Figure 10A:
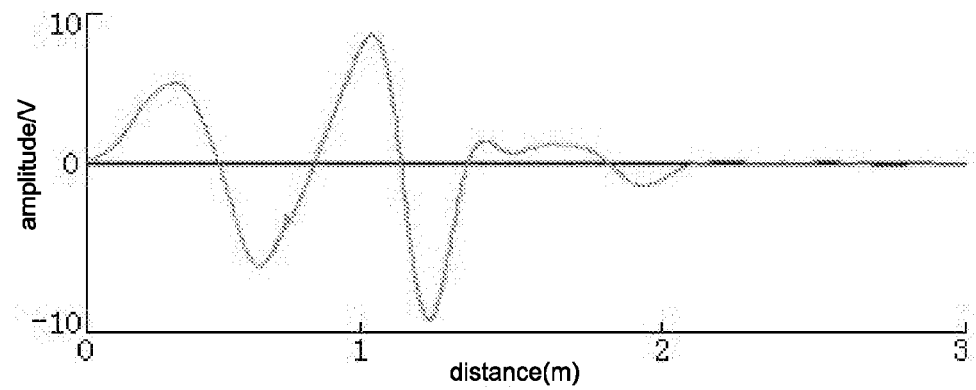
FIG. 10A and FIG. 10B are waveforms of antenna echo signals of transceiver antennas and bistatic antennas according to the preset invention.
Figure 10B:
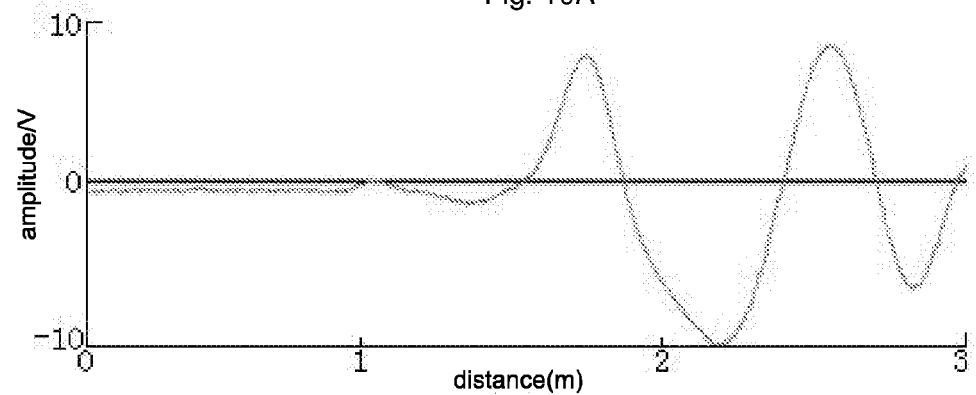

Referring to FIG. 10A and FIG. 10B of the drawings, a comparison of the echo signals obtained by the transceiver antenna and the receiving antenna are illustrated. A waveform of the echo signal obtained by the transceiver antenna is illustrated in FIG. 10A. A waveform of the echo signal obtained by the bistatic antenna is illustrated in a part (b) of the FIG. 10B, wherein the distance between the receiving antenna and the transmit antenna 1.5 m. Locations of the two signals are or 1 ns. The time windows are set to 20 ns. It can be concluded that: because the receiving and transmitting antennas in a transceiver antenna form are very close, the echo signals comprises medium reflected information within the whole time window; because the receiving and transmitting antennas in a bistatic antenna form are a distance from each other, a first half of the echo signals within the time window comprises a basically stable direct wave, and direct wave length depends on a time for the electromagnetic wave travels from the transmitter antenna directly to the receiving antenna, excluding any reflection information in the detection area. A second half of the echo signal comprises waveforms representing target reflection information.

Figure 11:
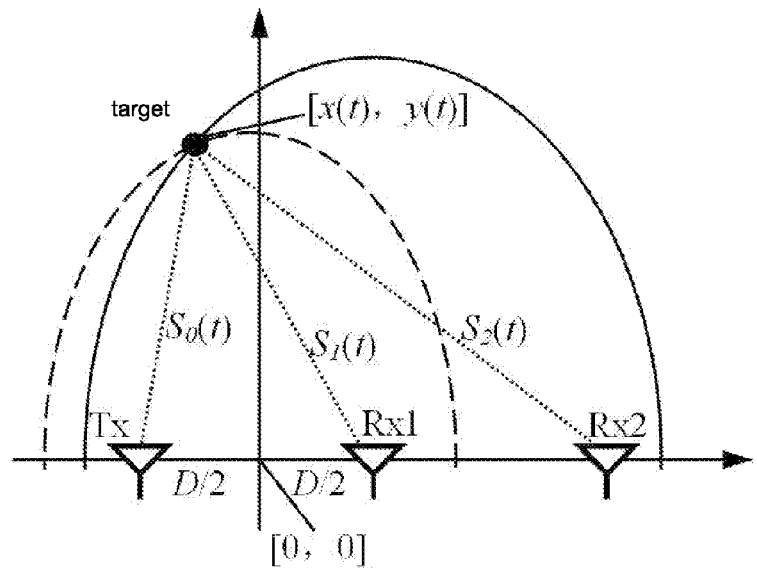
FIG. 11 is a sketch view of 2-dimensional target positioning of the multichannel system according to the preset invention.

Referring to FIG. 11 of the drawings, a sketch view of 2-dimensional target positioning of the multichannel system with the bistatic antenna according to the preset invention is illustrated.

The FIG. 11 is a sketch view of positioning a single target. The 2-dimensional positioning is realized with a transmitting antenna Tx and a set of receiving antennas (comprising two receiving antennas Rx1 and Rx2). A position of the target id identified by calculating a following electromagnetic wave route for reaching the receiving antennas after the electromagnetic wave transmitted by the transmitting antenna reaches the target and is reflected back by the target. A distance between the transmitting antenna Tx and the target is $S_0(t)$, a distance between the receiving antenna Rx1 and the target is $S_1(t)$, and a distance between the receiving antenna Rx2 and the target is $S_2(t)$. Times (travel times) for the electromagnetic wave transmitted by the Tx to reach the target and be reflected back from the target to reach the Rx1 and the Rx2 are respectively $\tau_1 = (S_0(t) + S_1(t))/c$ and $\tau_2 = (S_0(t) + S_2(t))/c$. Two ovals can be determined by the $\tau_1$ and $\tau_2$, focuses thereof are the transmitting antenna Tx and the corresponding receiving antenna Rx1 or Rx2. Thus, the position of the target is determined by a cross part of the two ovals. Calculation equation (7) and (10) of the ovals are as follows:

$$\left(\frac{x(t) + \frac{D}{2}}{a_1(t)}\right)^2 + \left(\frac{y(t)}{b_1(t)}\right)^2 = 1 \quad (7)$$

$$\left(\frac{x(t)+\frac{D}{2}}{a_2(t)}\right)^2 + \left(\frac{y(t)}{b_2(t)}\right)^2 = 1 \qquad (8)$$

The $2a_i$ is a long axis of the oval, which is also the route for the electromagnetic wave to be transmitted by the transmitting antenna and be reflected to the receiving antenna; the $2a_i$ is obtained by calculating the time $\tau_i$, a calculation formula thereof is illustrated as a following formula (9), wherein the i is 1 or 2, which is the order number of the antenna.

$$2a_i(t) = S_0(t) + S_i(t) = c\tau_i(t) \qquad (9)$$

The short axis $2b_i$ of the oval is obtained by calculating with a formula (10).

$$\left(\frac{D}{2}\right)^2 + b_i^2(t) = a_i^2(t) \qquad (10)$$

Accuracy of the above algorithm depends on the distance between the antennas, size of the target and accuracy of the time delay τi obtained by calculating the antenna echo signal. Therefore, a high-accuracy UWB-based radar unit is utilized. According to the preferred embodiment 5, highest accuracy of the multichannel UWB-based system is 4 ns/2048≈2 ps (picoseconds) in theory, converted distance accuracy is 2 ps×c=0.03 cm (centimeter), which satisfy an accuracy requirement.

5-3) Structure of an Antenna Array

Before an experiment, following conventional knowledge should be noticed:

(1) the transmitting antennas of the multichannel UWB-based system are not able to work together; otherwise, the transmitting antennas will interfered each other; therefore, only one transmitting antenna is utilized;

(2) with a single channel, only the distance of the target is able to be identified and the angle information is not obtained; for the 2-dimensional positioning of the target, two or more channels should be utilized; therefore, in the experiment, more than two receiving antenna are utilized for positioning;

(3) with a same positioning effect, a design with least antennas should be utilized for decreasing volume and weight of the system, increasing portability, and being conducive to popularization and application in the future; besides, decreasing of the antennas greatly simplifies the system sampling and computation and improves computation efficiency; and (4) because the 2-dimensional target positioning is needed instead of 3-dimensional imaging, the antennas are just arranged on a same horizontal level; for a certain lab detection platform, the antennas are just arranged in a same horizontal line.

Based on the above four points, the following experiment is provided.

5-3-1) a Number of the Receiving Antennas Selected

The two channels provide the positioning of the multiple stationary targets, but the results may comprise artifacts. Therefore, the projection signal of the third channel is utilized for confirming and eliminating the artifacts, wherein points where elliptic arcs of the projection signals of the three channels intersect are real locations of the target, which is proved in practical detection experiment. As a result, a transmitting antenna and three receiving antennas are finally selected.

5-3-2) Determination of a Position of the Transmitting Antenna

According to a statistics result of standing height and sitting height of normal adults, in order to ensure that the best detection results will be obtained no matter the target is standing or sitting, set-up height of the antennas are 1.2 m; that is to say, the transmitting antenna and three receiving antennas are all placed on horizontal line with a height of 1.2 m.

5-3-3) Determination of Positions of the Receiving Antennas

After the determination of a position of the transmitting antenna, the receiving antennas are placed adjacent to the transmitter antenna for forming a single channel system similar to a transceiver form. The channel is mainly used for distinguishing the target by distance. In order to ensure symmetry of angle resolution ratio within the detection area, the rest two receiving antennas are symmetrically arranged at both sides of the 1.2 m-high horizontal line with the transmitting antenna as the center, wherein the receiving antennas are respectively place a distance of 0.5 m 1.0 m and 1.5 m from the transmitting antenna. According to the experiment, the closer the distance is, the lower the target angle resolution ratio will be; the farther the distance is, the higher the target angle resolution ratio will be. That is to say, the distance between the receiving antenna and the central transmitting antenna is approximately inversely proportional to the target angle resolution ratio. If the distance is infinitesimal in such a manner that the receiving antennas are adjacent to the transmitting antenna, the effect of the three channels are the same and the three channels are only for multi-target distance distinction with no angle resolution ratio. According to the above experiment, for ensuring max angle resolution ratio, one of the receiver antenna is place adjacent to the transmitting antenna, while the other two receiving antenna are placed 1.5 m from the transmitting antenna, and symmetrically on both sides of the transmitting antenna.

5-3-4) Summary

A transmitting antenna and three receiving antennas are utilized, which is a least quantity of antennas needed for positioning, wherein the transmitting antenna is close to one of the receiving antennas and is placed in a center, the other receiving antennas are placed at two sides for forming a dumbbell-shaped structure. It can also be concluded from the experiment that the distance L between the receiving antenna and the central transmitting antenna is approximately inversely proportional to the target angle resolution ratio θ, namely L∝1/θ.

Preferred Embodiment 6

6-1) a Filtered Back Projection Reconstruction Algorithm

According to the preferred embodiment 6, a filtered back projection reconstruction method comprises correcting before back-projecting. As a result, more precise original density function is able to be obtained, wherein for each of the channels, calculated projection data are corrected at first, and then are back-projected to each pixel on a projection plane. And the original density function is reconstructed thereby.

First, the projection signal is corrected by averaging and normalizing.

A medians of the projection signal (comprising 100 points) of each of the channels is identified for setting values lower than the medians to zero without changing the rest; for ensuring that energy contribution weights of the projection signals of the three channels are the same for the 2-dimensional positioning image, the averaged signal is normalized by a formula (11):

$$r(t) = 2 \times \frac{e(t) - \min_{0 \le t \le T}[e(t)]}{\max_{0 \le t \le T}[e(t)] - \min_{0 \le t \le T}[e(t)]} \quad (11)$$

wherein the t is a time validate, the T is length of the projection signal, the e is an input, and the x is an output.

The projection signals of the three channels are back-projected to the detection area after being corrected.

Figure 12:
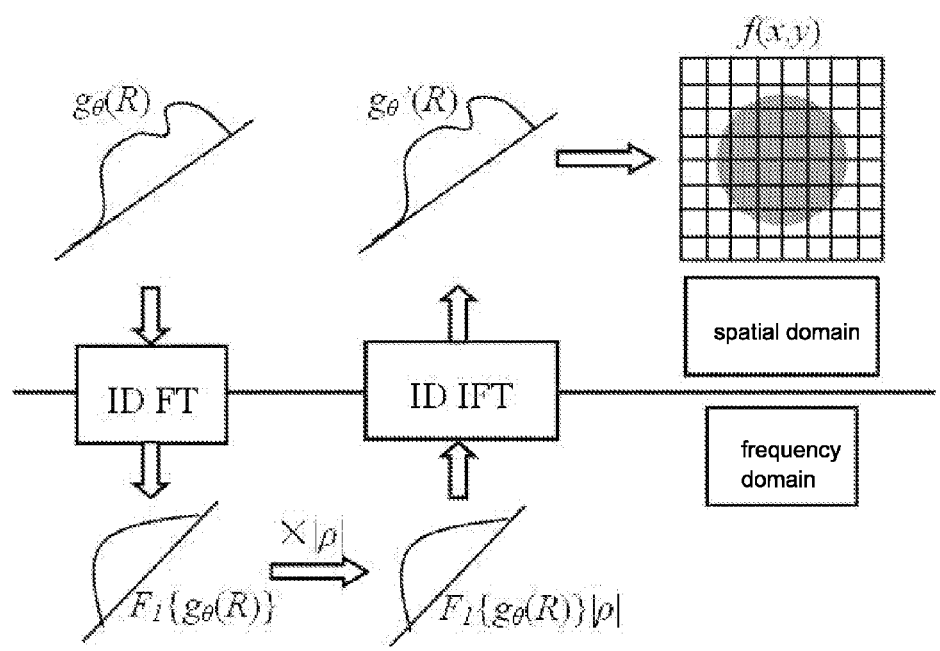
FIG. 12 is a sketch view of filtered back projection according to the preset invention.

Basic principles of the filtered back projection algorithm are: after a projection function (which is a 1-dimensional function) is extracted from the echo signal obtained by the receiving antenna, the 1-dimensional projection function is filtered for obtaining a modified projection function; then black projection computation is provided to the modified projection function for obtaining a density function. Referring to FIG. 12 of the drawings, an image reconstruction method of the filtered back projection according to the preset invention is illustrated.

The image reconstruction method comprises steps of:

a) applying 1-dimensional Fourier transform on the projection signals obtained by one of the antennas;

b) multiplying the transformed projection signals obtained in the step a) by a 1-dimensional weighting factor $|\rho|$;

c) applying 1-dimensional inverse Fourier transform on the multiplied projection signals obtained in the step b);

d) directly back-projecting the modified projection function obtained in the step c); and e) repeating the step a) to the step d) until the projection signals of each of the channels are back-projected.

According to a range of the breathing rate and comparison of a huge amount of experiments, the 1-dimensional weighting factor $|\rho|$ is finally defined as illustrated in a following equation (12):

$$\begin{cases} |\rho| = 1 & 0.08 \text{ Hz} < F_1\{g_\theta(t)\} < 0.7 \text{ Hz} \\ |\rho| = 0 & F_1\{g_\theta(t)\} < 0.08 \text{ Hz or } F_1\{g_\theta(t)\} > 0.7 \text{ Hz} \end{cases} \quad (12)$$

Compared to a reconstruction method that the back projection is provided before the modification, only the 1-dimensional Fourier transform is provided during the image reconstruction of the filtered back projection, in such a manner that the image reconstruction takes less time.

6-2) Smearing and an Elimination Method Thereof

Figure 13:
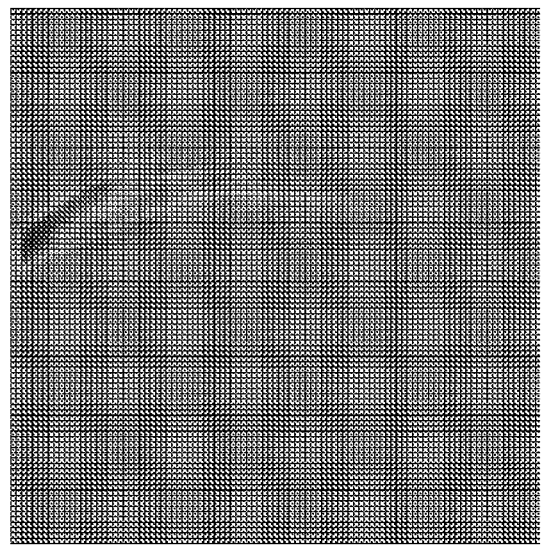
FIG. 13 is a result of positioning after smearing elimination (wherein a threshold is set to 150) according to the preset invention.

It can be concluded that the target position is obtained from the cross part of the ovals, but the smearing exists. For eliminating the smearing, a threshold is provided for pixel value of the 2-dimensional plane. Pixels with a value lower than the threshold is colored by a background color. Because the pixel values of 0~255 are corresponding to cool colors (blue) to warm colors (red) in a pseudo color image, the threshold is set to 150. That is to say, light green and above colors are displayed in the image and the pixels with a value lower than 150 is colored by a background color. Thereby, the smearing is eliminated and the position of the target is clearer. Referring to FIG. 13 of the drawings, a result of positioning after smearing elimination by setting the threshold according to the preset invention is illustrated.

Figure 14:
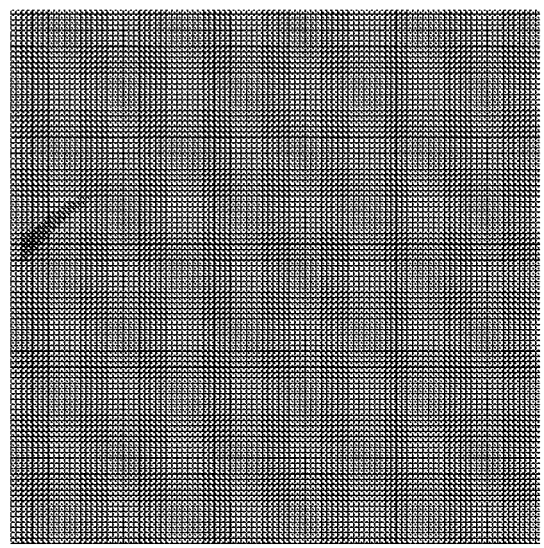
FIG. 14 is a result of positioning after smearing elimination (wherein a threshold is set to 230) according to the preset invention.

In the experiment, after raising the threshold, for example, to 230, the positioning image of the single target is clearer and positioning effect is more significant. Referring to FIG. 14 of the drawings, a result of positioning after smearing elimination with the threshold of 230 according to the preset invention is illustrated.

After the threshold is raised to 230, the position of the single target is clearer, the smearing is further eliminated and position accuracy is further improved. However, the threshold is not able to be raised without limits. If the threshold is raised to mush, the target with low energy will be missed during the detection of the multiple targets. After a plurality of experiments, in consideration of smearing elimination effect and not missing the target, the threshold is finally set to 150.

6-3) Position Results of the Filtered Back Projection Reconstruction Algorithm

Figure 15:
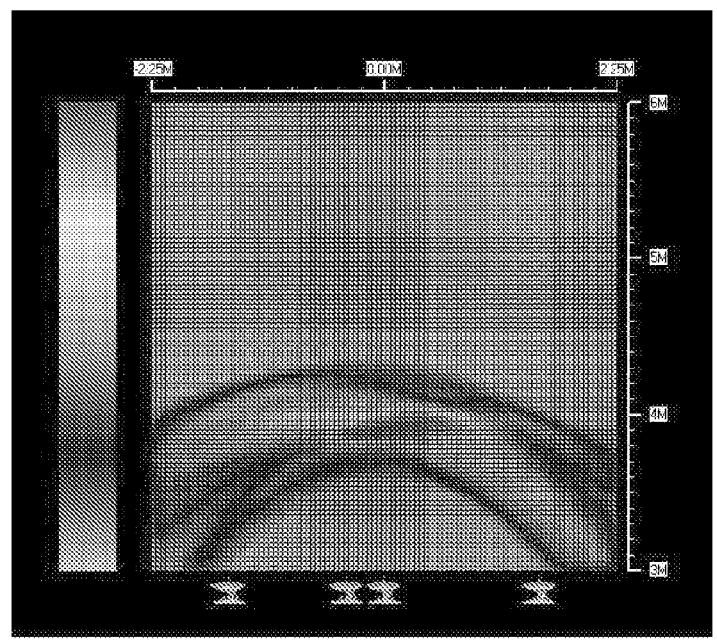
FIG. 15 is a result of positioning of a single target according to the preset invention.
Figure 16:
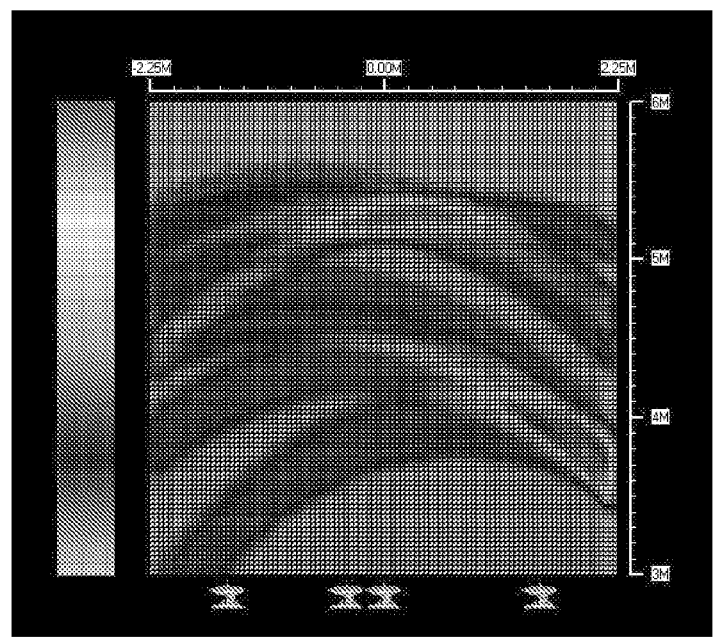
FIG. 16 is a result of positioning of double targets according to the preset invention.
Figure 17:
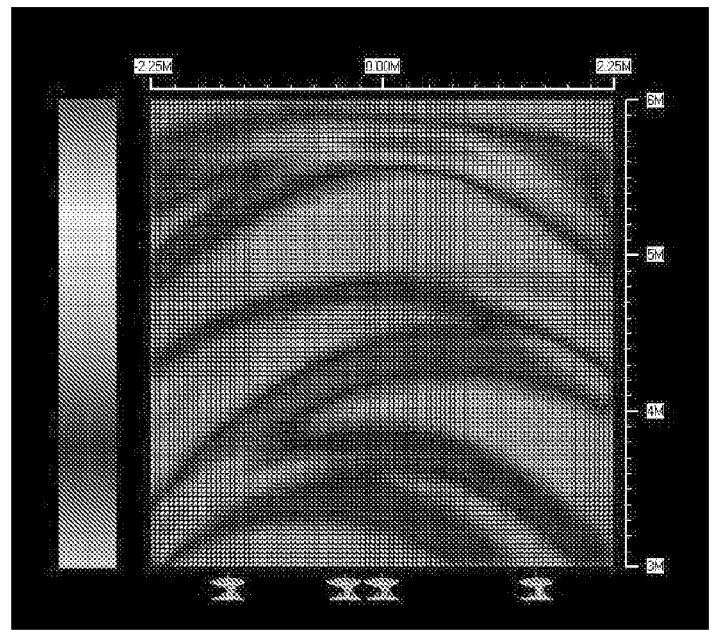
FIG. 17 is a result of positioning of triple targets according to the preset invention.

Through-wall detection and identification experiments of multichannel UWB-based radar life detector are respectively provided without target, with single target, with double targets and with triple targets (wherein the target are all standing stationary targets). The experiments are provided in a laboratory. According to a location of the laboratory, a left side of the results points to the south, a right side points to the north. Referring to FIG. 15, FIG. 16 and FIG. 17 of the drawings, results of positioning of the single target, the double targets and the triple targets with the filtered back projection reconstruction algorithm according to the preset invention are illustrated. The three images are not smearing-eliminated. Parameters thereof are: a signal position of 20 ns and a time window of 20 ns. According to calculation, the detection range is 3~6 m. Referring to the FIG. 15 of the drawings, the result of single target positioning is illustrated, wherein the actual position of the target is in a center with a distance of 4 m. Referring to the FIG. 16 of the drawings, the results of double targets positioning are illustrated, wherein the actual positions of the targets are respectively 30° in the north with a distance of 4 m and in a center with a distance of 5 m; wherein the target positions marked with the warm colors are consistent with actual positions. Referring to the FIG. 17 of the drawings, the results of triple targets positioning are illustrated, wherein the actual positions of the targets are respectively 30° in the south with a distance of 3 m, 30° in the north with a distance of 4 m and in a center with a distance of 5.5 m; wherein the target positions marked with the warm colors are also consistent with actual positions.

According to the above results of single, double, triple targets positioning results, up to three stationary standing human targets are able to be accurately identified and positioned through the wall with the filtered back projection reconstruction algorithm. Therefore, the filtered back projection algorithm is able to be applied in detection and positioning of multiple stationary targets with the multichannel radar Life detector.

Figure 18:
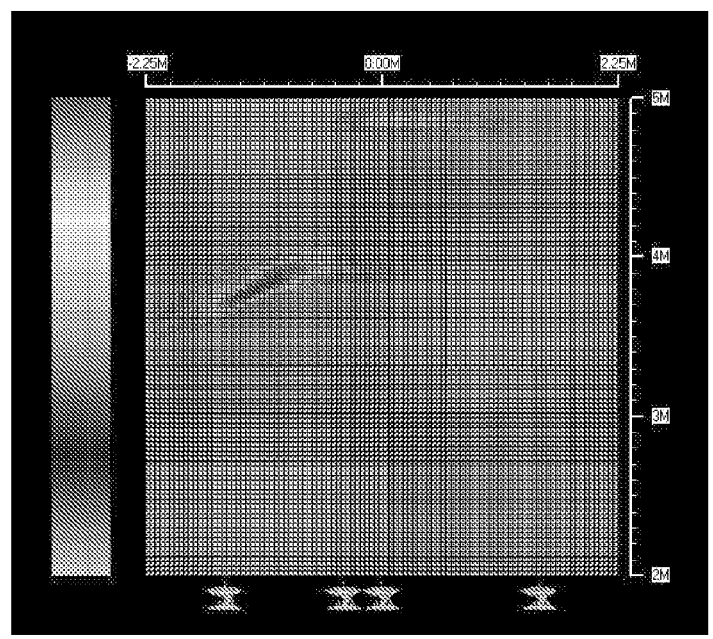
FIG. 18 is a result of positioning of double targets according to the preset invention (wherein the smearing elimination is provided).
Figure 19:
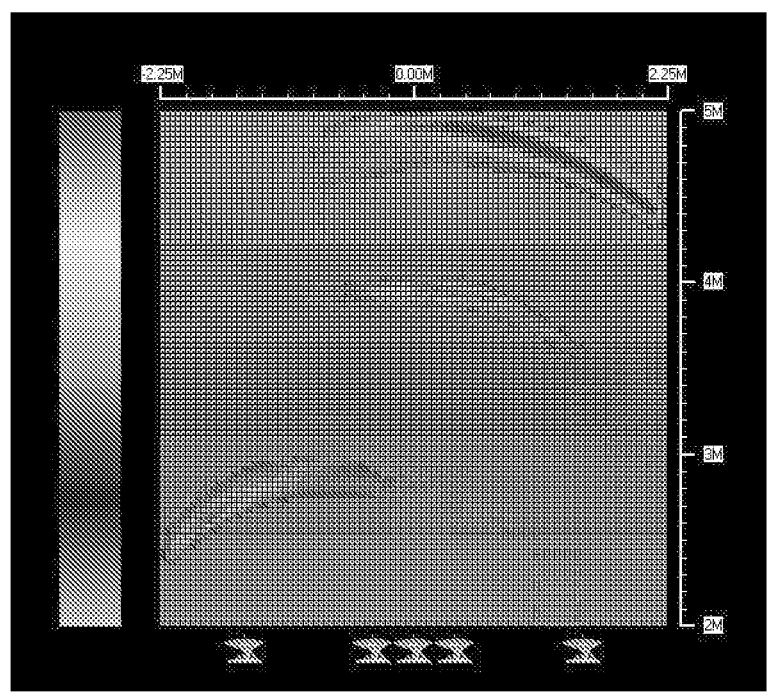
FIG. 19 is a result of positioning of triple targets according to the preset invention (wherein the smearing elimination is provided).

Referring to FIG. 18 and FIG. 19 of the drawings, results of the positioning of the double targets and the triple targets according to the preset invention are respectively illustrated. Parameters are: a signal position of 15 ns, a time window of 20 ns, and a detection range of 2~5 m. Referring to the FIG. 18 of the drawings, the results of the double targets positioning are illustrated, wherein the actual positions of the targets are respectively 20° in the south with a distance of 4 m and in a center with a distance of 5 m. Referring to the FIG. 19 of the drawings, the results of triple targets positioning are illustrated, wherein the actual positions of the targets are respectively 30° in the south with a distance of 3 m, in a center with a distance of 4 m and 20° in the north with a distance of 5 m. After the smearing elimination, the red area of the result is clearer as well as the targets. Besides, the resolution ratio of the targets is also improved.

6-4) Efficiency Evaluation of the Filtered Back Projection Reconstruction Algorithm The efficiency evaluation of the filtered back-projection algorithm is provided on a test platform of the multichannel UWB-based radar life detector. The structure of the antenna array is long dumbbell-shaped. Main parameters of the system are: the signal position of 15 ns and the time window of 20 ns. All the experiment data are acquired through a 30 cm-thick brick wall. The targets are randomly selected from 16 volunteers according to a requirement of target quantity. All of the experiment data are acquired when the targets are stationary and standing, in such a manner that stationary human target detection experiment is provided. Target distribution is defined as follows: longitudinal distance between any two targets is at least 0.5 m while the horizontal angle is at least 20°.

17 sets of through-wall data with no target are acquired. According to the above classification, the results of data acquired are analyzed. Because of no target, no target is missed or mistaken. Statistical results are illustrated in Table 4.

TABLE 4 accuracy of positioning through a 30 cm-thick brick wall with no target data

|  | right | wrong | missed | mistaken | total |
|---|---|---|---|---|---|
| set number of signals | 16 | 1 | 0 | 0 | 17 |
| percentage | 94% | 6% | 0% | 0% | 100% |

48 sets of through-wall data with the single target are acquired, wherein the targets are divided into four groups such as 30° in the south with a distance of 2 m, in a center with a distance of 2 m, 30° in the north with a distance of 2 m; 30° in the south with a distance of 3 m, in a center with a distance of 3 m, 30° in the north with a distance of 3 m; 20° in the south with a distance of 4 m, in a center with a distance of 4 m, 20° in the north with a distance of 4 m; and 20° in the south with a distance of 5 m, in a center with a distance of 5 m, 20° in the north with a distance of 5 m. Totally, 48 sets of the data are acquired. According to the above classification, the results of data acquired are analyzed. Statistical results are illustrated in Table 5.

TABLE 5 accuracy of positioning through a 30 cm-thick brick wall with single target

|  | right | wrong | missed | mistaken | total |
|---|---|---|---|---|---|
| set number of signals | 39 | 7 | 2 | 0 | 48 |
| percentage | 81% | 15% | 4% | 0% | 100% |

60 sets of through-wall data with the double targets are acquired. Two targets are randomly arranged within a detection area of 2~5 m behind the wall while other conditions satisfy the above requirements, wherein the targets are stationary and standing with different distance and different angles. According to the above classification, the results of data acquired are analyzed. Statistical results are illustrated in Table 6.

TABLE 6 accuracy of positioning through a 30 cm-thick brick wall with double target

|  | right | wrong | missed | mistaken | total |
|---|---|---|---|---|---|
| set number of signals | 50 | 9 | 3 | 1 | 60 |
| percentage | 78% | 15% | 5% | 2% | 100% |

85 sets of through-wall data with the triple target are acquired. Three targets are randomly arranged within a detection area of 2~5 m behind the wall while other conditions satisfy the above requirements, wherein the targets are stationary and standing with different distance and different angles. Because the identification and positioning are provided only for three targets, no target is mistaken. According to the above classification, the results of data acquired are analyzed. Statistical results are illustrated in Table 7.

TABLE 7 accuracy of positioning through a 30 cm-thick brick wall with double target

|  | right | wrong | missed | mistaken | total |
|---|---|---|---|---|---|
| set number of signals | 57 | 0 | 23 | 5 | 85 |
| percentage | 67% | 0% | 27% | 6% | 100% |

According to the statistical results of identification and positioning of the data of the targets with the different distribution of the number of different target, the accuracy of the 17 sets of the data identified by the filtered back projection algorithm is 94%, the accuracy of the 48 sets of the data of the single target is 81%, the accuracy of the 60 sets of the data of the double targets is 78%, and the accuracy of the 85 sets of the data of the triple targets is 67%. It can be concluded that, the accuracy of filtered back projection algorithm for identifying the data of no target is the highest, while the accuracy of identifying the data of the triple targets is the lowest.

Overall, the filtered back projection reconstruction algorithm is able to be applied on identification and positioning of up to three stationary human targets.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A multichannel UWB-based radar life detector, comprising:
a UWB bio-radar front-end; and
a calculation unit;
wherein said UWB bio-radar front-end comprises:
a transmitting antenna;
three receiving antennas;
a pulse oscillator;
an electromagnetic pulse generator; and
a sampling integrator;
wherein said transmitting antenna respectively forms channels with each of the receiving antennas in such a manner that three said channels are formed; said pulse oscillator generates a pulse signal, said pulse signal stimulates said electromagnetic pulse generator for generating a narrow pulse and transmitting said narrow pulse through said transmitting antenna; a reflected signal of said narrow pulse is sent to said sampling integrator through said receiving antenna; said pulse signal generated by said pulse oscillator also passes through a time-delay circuit and a range gate generator for generating a range gate and selecting said reflected signal; said reflected signal is integrated by said sampling integrator and weak signals are detected; said weak signals are amplified by an amplifier and filtered by a filter for obtaining three radar echo signals; said radar echo signals are sampled by a high-speed A/D data acquisition card and sent to said calculation unit for analysis, in such manner that biological information and 2-dimensional position information of multiple human targets are finally obtained.

2. The multichannel UWB-based radar life detector, as recited in claim 1, wherein said transmitting antenna is close to one of said receiving antennas and is placed in a center, said other receiving antennas are placed at two sides for forming a dumbbell-shaped structure.

3. The multichannel UWB-based radar life detector, as recited in claim 1, wherein said calculating unit comprises:
a signal integration module;
a signal decomposition and reconstruction module;
a digital filtering module;
a digital differential module;
a spatial frequency analysis module; and
a filtered back projection positioning module;
wherein said signal integration module integrates said radar echo signals by distance; said signal decomposition and reconstruction module decomposes and reconstructs said integrated radar echo signals for forming three target echo signals and three distance signals; said digital filtering module and said digital differential module provide digital filtering and digital differential to said target echo signals; said spatial frequency analysis module analyzes spatial frequency according to said filtered and differentiated target echo signals as well as said distance signals for obtaining three projection signals of said targets; said filtered back projection positioning module identifies said 2-dimensional position information of said targets according to said projection signals and forms an image.

4. The multichannel UWB-based radar life detector, as recited in claim 3, further comprising: a projection signal pretreatment module for averaging and normalizing said projection signals before sending said pretreated projection signals to said filtered back projection positioning module.

5. The multichannel UWB-based radar life detector, as recited in claim 4, wherein said filtered back projection positioning module comprises:
a 1-dimensional Fourier transform module;
a 1-dimensional weighting factor module;
a 1-dimensional inverse Fourier transform module; and
a direct back projection module;
wherein said 1-dimensional Fourier transform module applies 1-dimensional Fourier transform on said pretreated projection signals; said 1-dimensional weighting factor module multiplies said transformed projection signals by a 1-dimensional weighting factor $|\rho|$; said 1-dimensional inverse Fourier transform module applies 1-dimensional inverse Fourier transform on said multiplied projection signals; said direct back projection module directly projects said inversely transformed projection signals.

6. The multichannel UWB-based radar life detector, as recited in claim 5, wherein said 1-dimensional weighting factor is finally defined as:

$$\begin{cases} |\rho| = 1 & 0.08 \text{ Hz} < F_1\{g_\theta(t)\} < 0.7 \text{ Hz} \\ |\rho| = 0 & F_1\{g_\theta(t)\} < 0.08 \text{ Hz or } F_1\{g_\theta(t)\} > 0.7 \text{ Hz} \end{cases},$$

wherein $g_\theta(t)$ is said pretreated projection signal of one of said channels, $F_1\{g_\theta(t)\}$ is said transformed projection signal.

7. The multichannel UWB-based radar life detector, as recited in claim 3, further comprising: a smearing elimination module for eliminating smearing of said image formed by said filtered back projection positioning module.

8. The multichannel UWB-based radar life detector, as recited in claim 7, wherein said smearing is eliminated by a method comprising: presetting a threshold of pixel value in a 2-dimensional display area, and coloring pixels with a value lower than t threshold by a background color.

9. The multichannel UWB-based radar life detector, as recited in claim 7, wherein said image is displayed in a 2-dimensional pseudo color mode, distance and angle information is also displayed for positioning said multiple targets and displaying detection results.

10. A 2-dimensional positioning method of a multichannel UWB-based radar life detector for positioning the multiple human targets, wherein the multichannel UWB-based radar life detector comprises: a transmitting antenna and three receiving antennas for forming three radar echo channels; wherein the 2-dimensional positioning method comprises steps of:
a1) amplifying weak life signals of stationary human bodies by the channels, processing radar echo signals by distance with an 8-point integration method with an interval of 4 points; then breaking the integrated signals for decomposition and reconstruction in such a manner that target echo signals and three distance signals are formed; providing digital filtering and digital differential to the target echo signals for amplifying the weak but useful life signals;

a2) 1-dimensionally distinguishing the signals by distance, analyzing spatial frequency according to the filtered and differentiated target echo signals as well as the distance signals for obtaining three projection signals of the targets in the three channels; and a3) identifying the 2-dimensional position information of the targets according to the projection signals, and forming an image.

11. The 2-dimensional positioning method, as recited in claim 10, wherein the transmitting antenna is close to one of the receiving antennas and is placed in a center, the other receiving antennas are placed at two sides for forming a dumbbell-shaped structure.

12. The 2-dimensional positioning method, as recited in claim 10, wherein the step a1) specifically comprises steps of:

a11) respectively integrating the radar echo signals by distance;

a12) decomposing and reconstructing the integrated radar echo signals for forming the three target echo signals and the three distance signals;

a13) providing the digital filtering and the digital differential to the target echo signals; and a14) analyzing the spatial frequency according to the filtered and differentiated target echo signals as well as the distance signals for obtaining the three projection signals of the targets.

13. The 2-dimensional positioning method, as recited in claim 12, further comprising: a step of pretreating the projection signals, which is provided before the step a2), for averaging and normalizing the projection signals.

14. The 2-dimensional positioning method, as recited in claim 13, wherein the step a3) specifically comprises steps of:

a31) applying 1-dimensional Fourier transform on the pretreated projection signals;

a32) multiplying the transformed projection signals by a 1-dimensional weighting factor $|\mu|$;

a33) applying 1-dimensional inverse Fourier transform on the multiplied projection signals; and a34) directly projecting the inversely transformed projection signals.

15. The 2-dimensional positioning method, as recited in claim 14, wherein the 1-dimensional weighting factor $|\rho|$ in the step a32) is finally defined as:

$$\begin{cases} |\rho| = 1 & 0.08 \text{ Hz} < F_1\{g_\theta(t)\} < 0.7 \text{ Hz} \\ |\rho| = 0 & F_1\{g_\theta(t)\} < 0.08 \text{ Hz or } F_1\{g_\theta(t)\} > 0.7 \text{ Hz} \end{cases},$$

wherein $g_\theta(t)$ is the pretreated projection signal of one of the channels, $F_1\{g_\theta(t)\}$ is the transformed projection signal.

16. The 2-dimensional positioning method, as recited in claim 10, further comprising: a smearing elimination step for eliminating smearing of the image.

17. The 2-dimensional positioning method, as recited in claim 16, wherein the smearing is eliminated by a method comprising: presetting a threshold of pixel value in a 2-dimensional display area, and coloring pixels with a value lower than the threshold by a background color.

18. The 2-dimensional positioning method, as recited in claim 16, wherein the image is displayed in a 2-dimensional pseudo color mode, distance and angle information is also displayed for positioning the multiple targets and displaying detection results.

* * * * *